United States Patent
Luzbetak et al.

(10) Patent No.: US 7,780,201 B2
(45) Date of Patent: Aug. 24, 2010

(54) TUBE CONNECTOR WITH THREE PART CONSTRUCTION AND LATCHING COMPONENT

(75) Inventors: Mark A. Luzbetak, Kildeer, IL (US); Donald C. Walker, Mundelein, IL (US)

(73) Assignee: Medela Holding AG, Baar (CH)

( * ) Notice: Subject to any disclaimer, the term of this patent is extended or adjusted under 35 U.S.C. 154(b) by 65 days.

(21) Appl. No.: 11/581,210

(22) Filed: Oct. 13, 2006

(65) Prior Publication Data

US 2008/0090445 A1 Apr. 17, 2008

(51) Int. Cl.
*F16L 39/00* (2006.01)

(52) U.S. Cl. ..................................... 285/321

(58) Field of Classification Search ................ 439/271; 285/307, 308, 313, 321, 347; 604/74
See application file for complete search history.

(56) References Cited

U.S. PATENT DOCUMENTS

| | | | |
|---|---|---|---|
| 2,812,958 A | 11/1957 | Rogers | |
| 3,245,703 A | 4/1966 | Manly | |
| 3,434,746 A | 3/1969 | Watts | |
| 3,552,778 A | 1/1971 | Muller | |
| RE28,786 E | 4/1976 | MacDonald | |
| 4,029,105 A | 6/1977 | Faust | |
| 4,152,017 A | 5/1979 | Abramson | |
| 4,322,018 A | 3/1982 | Rutter | |
| 4,580,816 A | 4/1986 | Campbell et al. | |
| 4,610,468 A | 9/1986 | Wood | |
| 4,611,837 A | 9/1986 | Aleck | |
| 5,226,682 A | 7/1993 | Marrison et al. | |
| 5,257,833 A | 11/1993 | McNaughton et al. | |
| 5,507,535 A | 4/1996 | McKarmey et al. | |
| 5,720,722 A * | 2/1998 | Lockridge | 604/74 |
| 5,797,627 A | 8/1998 | Salter et al. | |
| 5,891,085 A | 4/1999 | Lilley et al. | |
| 6,419,281 B1 | 7/2002 | Salomon-Bahls et al. | |
| 6,423,053 B1 | 7/2002 | Lee | |
| 6,467,817 B1 | 10/2002 | Rhyman | |
| 6,585,695 B1 * | 7/2003 | Adair et al. | 604/183 |
| 6,676,171 B2 | 1/2004 | Bucher et al. | |
| 6,767,034 B2 | 7/2004 | Le Clinche | |
| 6,964,434 B2 | 11/2005 | Beck et al. | |
| 7,198,611 B2 * | 4/2007 | Connell et al. | 604/30 |
| 7,232,419 B2 * | 6/2007 | Castellanos | 604/29 |
| 2005/0043677 A1 | 2/2005 | Kelly et al. | |
| 2005/0057042 A1 | 3/2005 | Wicks | |
| 2005/0189765 A1 | 9/2005 | Maunder et al. | |

* cited by examiner

*Primary Examiner*—Chandrika Prasad
(74) *Attorney, Agent, or Firm*—McDonnell Boehnen Hulbert & Berghoff LLP

(57) ABSTRACT

A connector for connecting a tube within a receptacle. A latching component fits within the receptacle, and receives a plug member to which the tube is connected. One end of receptacle is adapted, for instance, to be attached to a tube on a motor drive unit of a breast pump assembly, or formed integrally therewith. The opposite end of receptacle receives components of the connector therein. The plug member is inserted into the latching component and has means thereon that engage corresponding means on the latching component such that the plug member is releasably secured within the latching component in a rotatable manner.

20 Claims, 15 Drawing Sheets

TUBE CONNECTOR WITH THREE PART CONSTRUCTION AND LATCHING COMPONENT

FIELD OF THE INVENTION

The present invention relates generally to tubing connectors, and more particularly in one aspect to a breast pump assembly including an improved connector for air tubing.

BACKGROUND OF THE INVENTION

Breast pumps are well known, and generally comprise a hood or shield that fits over the breast, a vacuum pump connected to the hood for generating an intermittent vacuum (or negative pressure) within the breastshield, and a receptacle for expressed milk. Negative pressure is pressure below atmospheric pressure; positive pressure has also sometimes been used in breast pumps. Typically, the intermittent suction action of the vacuum pump serves to pull on the breast and nipple and thereby express milk. The milk flows from the hood, through a conduit structure and into a collection container, such as a baby bottle, for storage and later use.

Breast pumps can be manually or electrically operated. In manually operated breast pump assemblies, the intermittent vacuum is typically generated by means of a piston-type or other hand drivable pump that attaches directly to the breast pump assembly. The intermittent pressure (e.g., vacuum) in motor-driven breast pump assemblies is typically derived from a motor drive unit that is separate from the breastshield and breast pump assembly. The vacuum is accordingly transmitted to the breastpump assembly through plastic tubing. The plastic tubing is often attached to one or both of the motorized pump and/or the breast pump assembly by use of a connector.

Because of the transfer of air throughout the breast pump assembly, the connector provides an airtight seal. Additionally, the user should be able to easily manipulate the connector in order to hook up the components and disconnect them repeatedly. Prior art connectors have used raw tubing inserted over a protruding stem, or a pair of tapered cylindrical male and female surfaces to provide the connection and seal. These methods really do not give the user any "positive feedback" that the connection has been made, and sometimes require significant effort to make or break the connection. Another issue with some of these prior art connectors is that they can lead to the tubing bending and even kinking at the connection point if the user strains the tubing through movement during pumping.

Accordingly, there is a demand for a connector that provides positive feedback to the user that the connection is made, allows for ease of connection, and that allows for some way to better avoid kinking of the tubing. The present invention satisfies this demand.

SUMMARY OF THE INVENTION

An object of the present invention is to provide a tubing connector that gives positive feedback to a user that a solid connection has been made.

Another object of the present invention is to provide a tubing connector for connecting two tubular objects, for instance, that allows for the making or breaking of a connection without significant effort.

Still another object of the present invention is to provide a tubing connector that allows rotation of the connection to avoid kinking.

One embodiment of the present invention provides a tubing connector for connecting two tubular objects such as a tube end that fits in a port (or socket or well). The tubing connector has a receptacle (the port, socket or well) sized and shaped to receive a plug member (on the tube end) therein. The receptacle has an annular groove on its interior surface. The plug member is secured within the receptacle by a latching component, which in one form is a sleeve that fits in the receptacle with a part that is received in the receptacle annular groove to join the latching component and the receptacle, and fits around the plug member when the latter is pushed within the latching component within the receptacle. The latching component has at least one resilient rib extending into the receptacle interior. The plug member has an annular groove therein that engages with the rib on the latching component to secure the plug member within the latching component in a rotatable manner.

In the foregoing embodiment, the latching component is initially separate from the receptacle, and is first placed on the plug then received within the receptacle; this provides a "retrofit" arrangement. In the alternative, the latching component could be made integral with the receptacle, or previously assembled therein, so that all one needs to do is insert the plug.

In another embodiment, the interengaging members are reversed, such that there is a circumferential ridge on the plug's exterior surface that engages an annular groove on the interior surface of the receptacle, or on the latching component secured within the receptacle.

Yet another objective for the invention is to better assure that only certain components can be connected together, such as only particular types of breast pumps being connected to a particular pressure source. Breast pump assemblies can come in many shapes and sizes. The amount of volume within these pump assemblies can vary greatly insofar as "dead" volume is concerned, i.e., the air that must be initially moved by the vacuum source. There is often concern that the proper breast pump assembly for a given pressure source be used, since the two may be specifically designed for use together, and some other breast pump assembly not so adapted may present undesirable issues.

These, together with other objects and advantages will be further understood in the details of the construction and operation of the invention as more fully hereinafter described, reference being had to the accompanying drawings, forming a part hereof, wherein like numerals refer to like parts throughout, in which:

DETAILED DESCRIPTION OF EMBODIMENTS OF THE INVENTION

The tubing connector of the present invention will be described herein in use in a breast pump assembly, but it is contemplated that the tubing connector of the present invention can be used in any device that may benefit from this type of connector.

Figure 1:
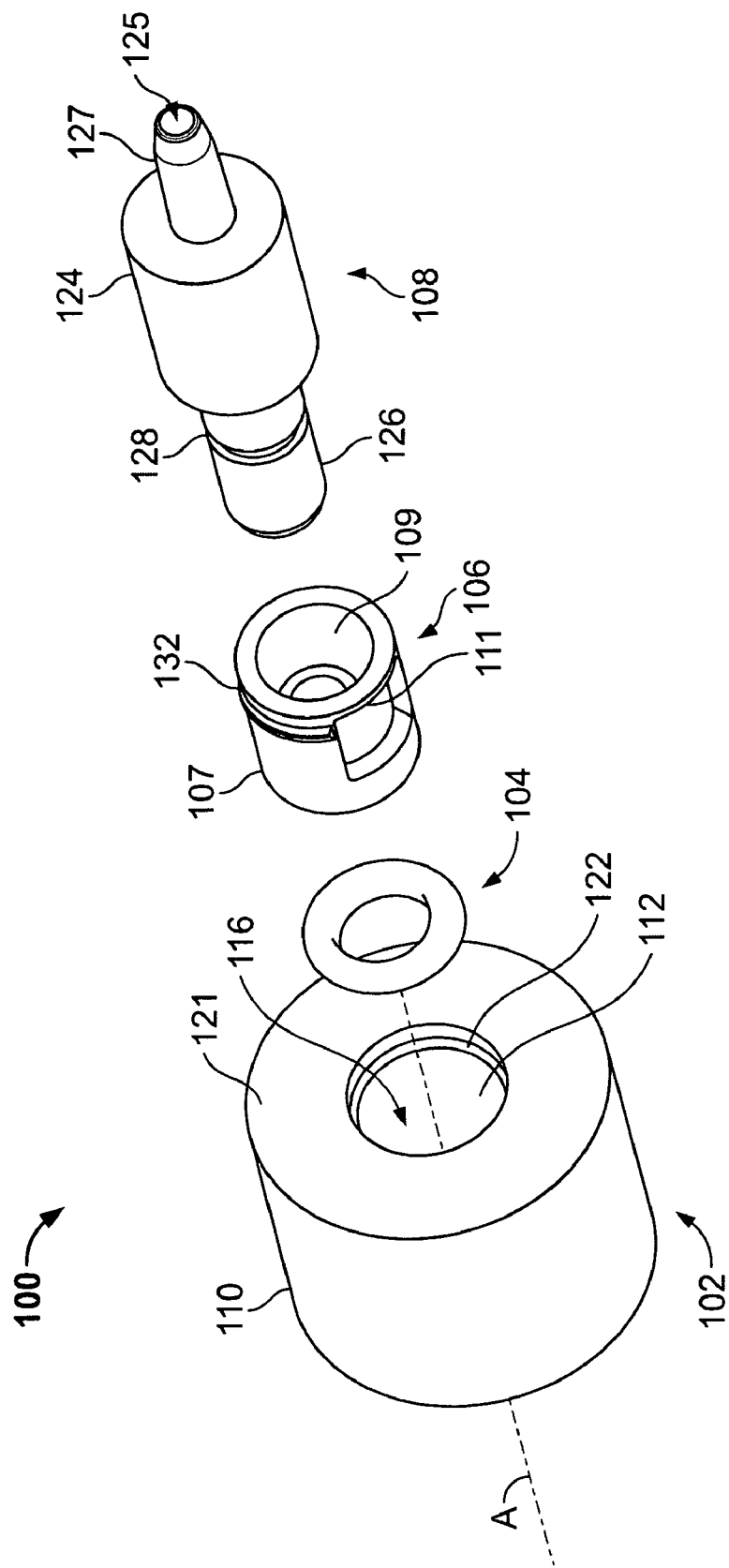
FIG. 1 is an exploded perspective view of an embodiment of a tube connector according to the present invention.
Figure 2:
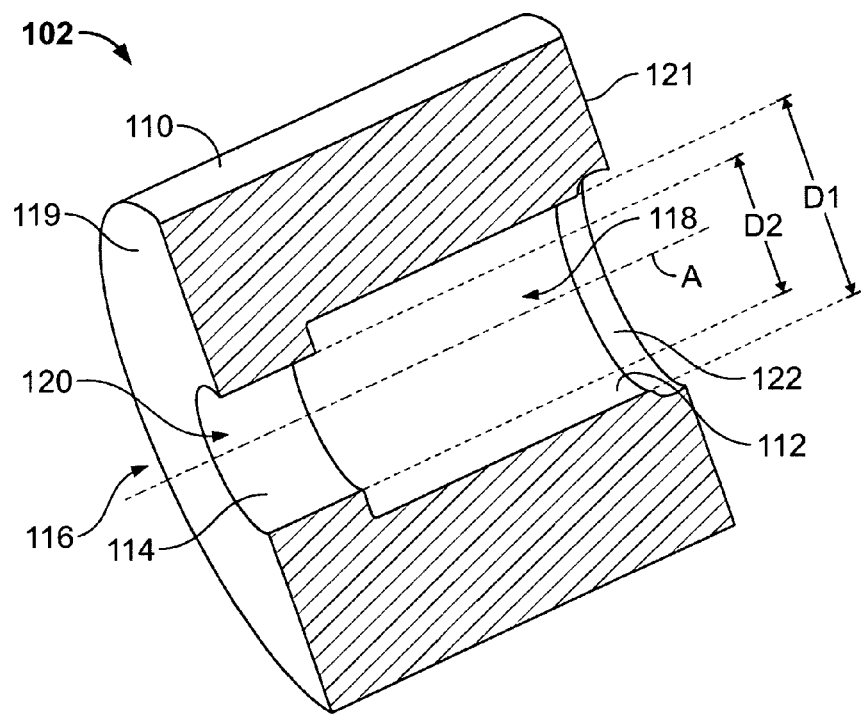
FIG. 2 is a perspective view of the receptacle portion of the tube connector of FIG. 1 according to the present invention.

FIG. 1 is an exploded view of a first embodiment of a tubing connector 100 according to the present invention. The tubing connector 100 includes a receptacle 102, a sealing ring 104, a latching component 106 and a plug member 108. As shown in FIG. 2, receptacle 102 has an exterior surface 110, a first interior surface 112 and a second interior surface 114, the first and second interior surfaces 112, 114 define a bore 116 therethrough.

It will be understood and seen herein, that the receptacle 102 is not necessarily a separate piece as depicted, but is more typically made integral with something within which the plug 108 is to connect. Receptacle 102 may therefore be a piece that is assembled to, for example, a motor drive as shown hereafter, or could be formed integral therewith. "Receptacle" is therefore used to generally also refer to a well, socket, orifice and the like.

Figure 6:
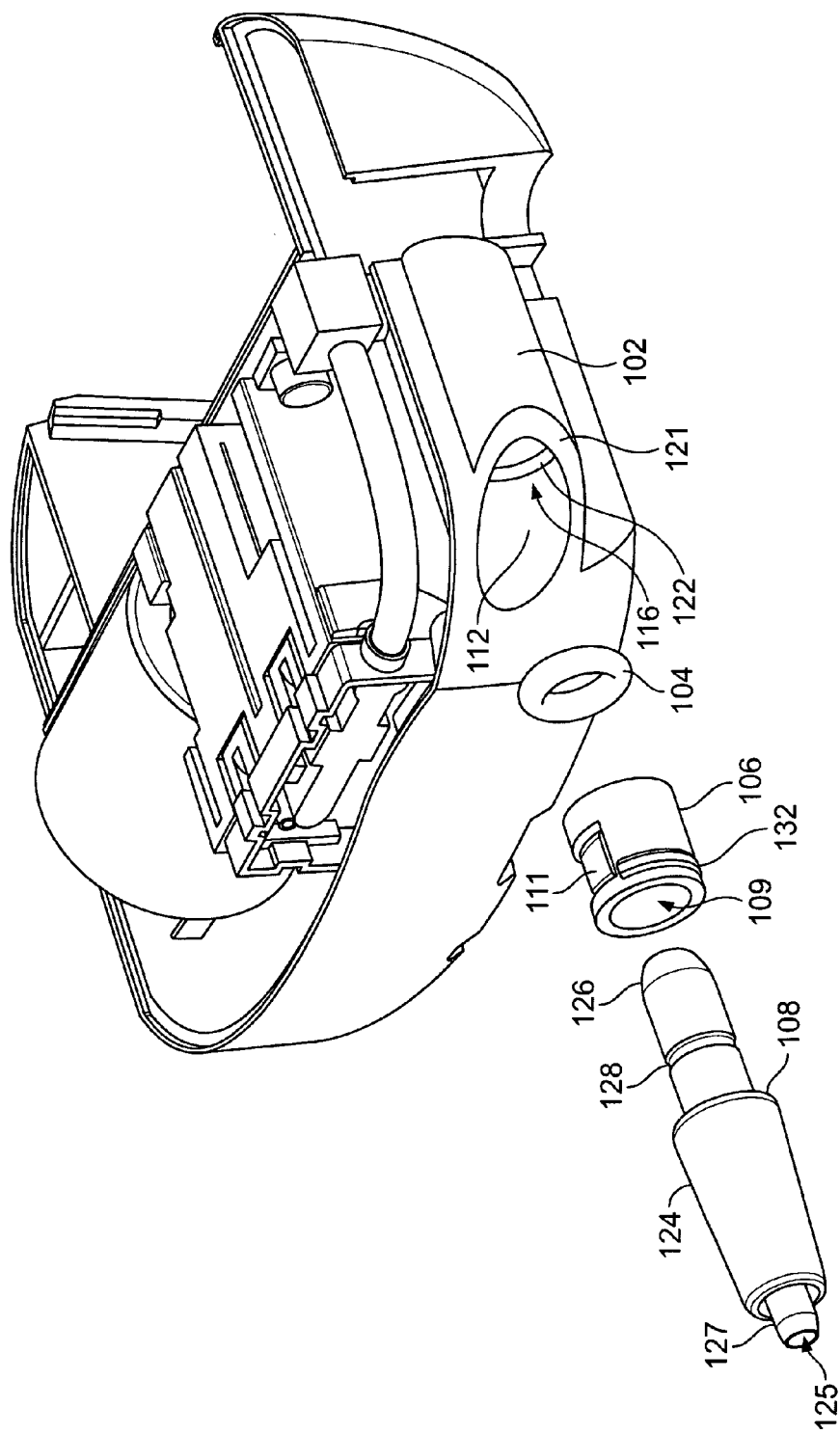
FIG. 6 is an exploded view of the tube connector of FIG. 1 and a motor drive unit according to the present invention.
Figure 7:
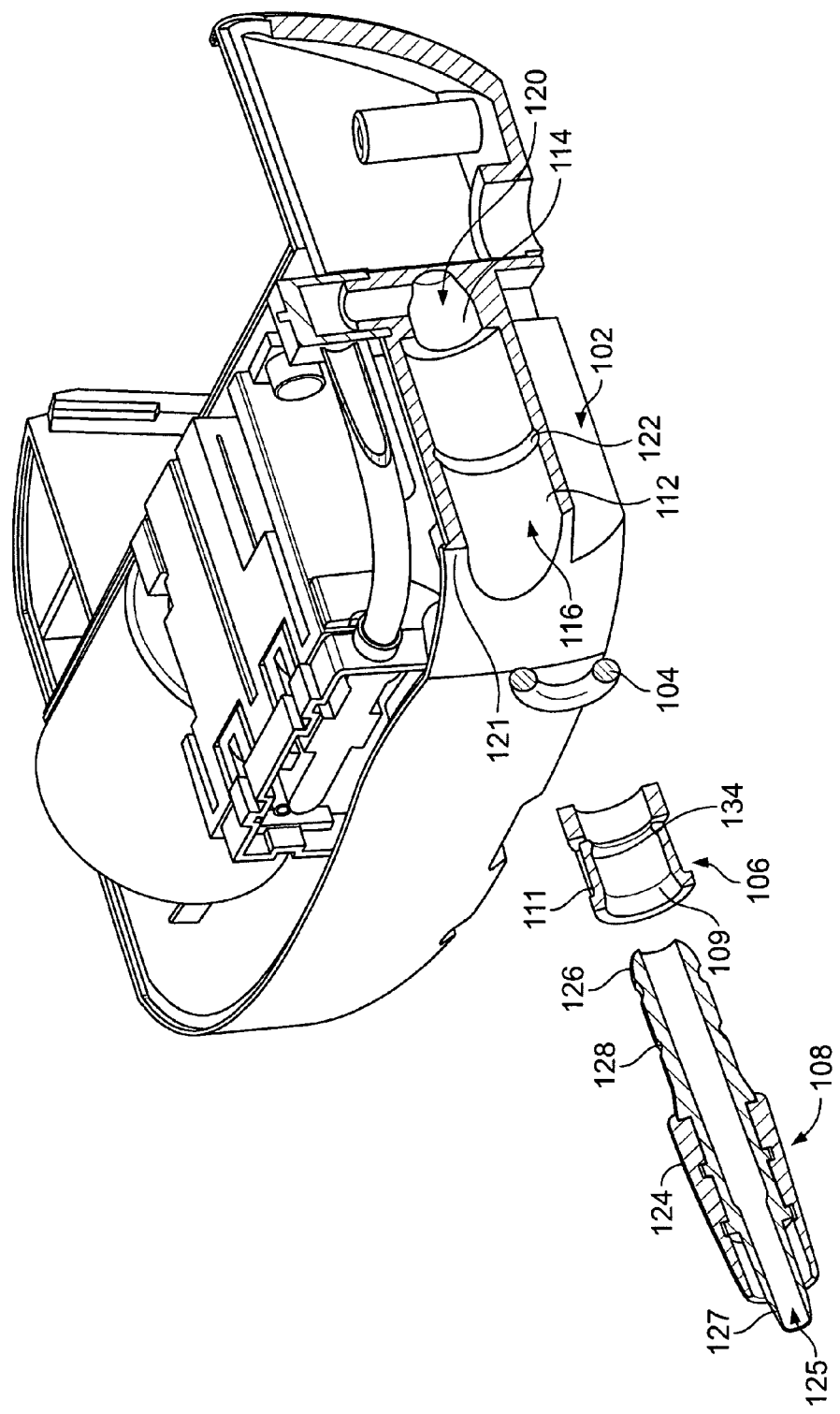
FIG. 7 is an exploded sectional view of the tube connector of FIG. 1 and a motor drive unit according to the present invention.
Figure 8:
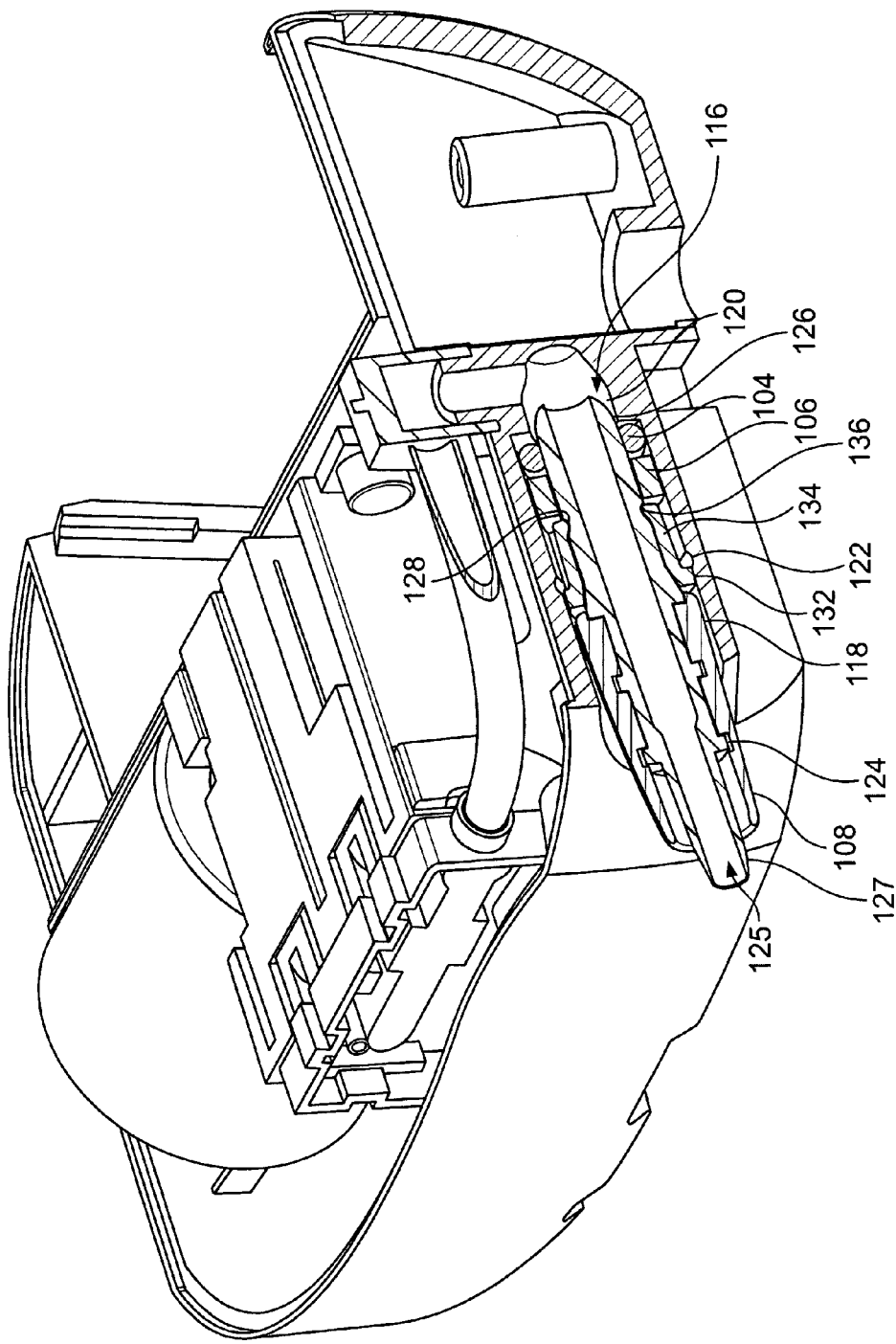
FIG. 8 is an assembled sectional view of the tube connector of FIG. 1 and a motor drive unit according to the present invention.

Referring to FIG. 2, an axis A extends into bore 116. Bore 116 has a first portion 118 defined by first interior surface 112 and a second portion 120 defined by second interior surface 114. First portion 118 has a first diameter D1 and second portion 120 has a second diameter D2. The first interior surface 112 further includes a circumferential groove or channel 122. Receptacle 102 includes two ends 119, 121. The first end 119 of receptacle 102 is adapted, for instance, to be connected to a motor drive unit of a breast pump assembly, or formed integrally therewith, as shown in FIGS. 6-8. The second end 121 of receptacle 102 receives other components of a tube connector therein, as will be described in detail below.

Figure 3:
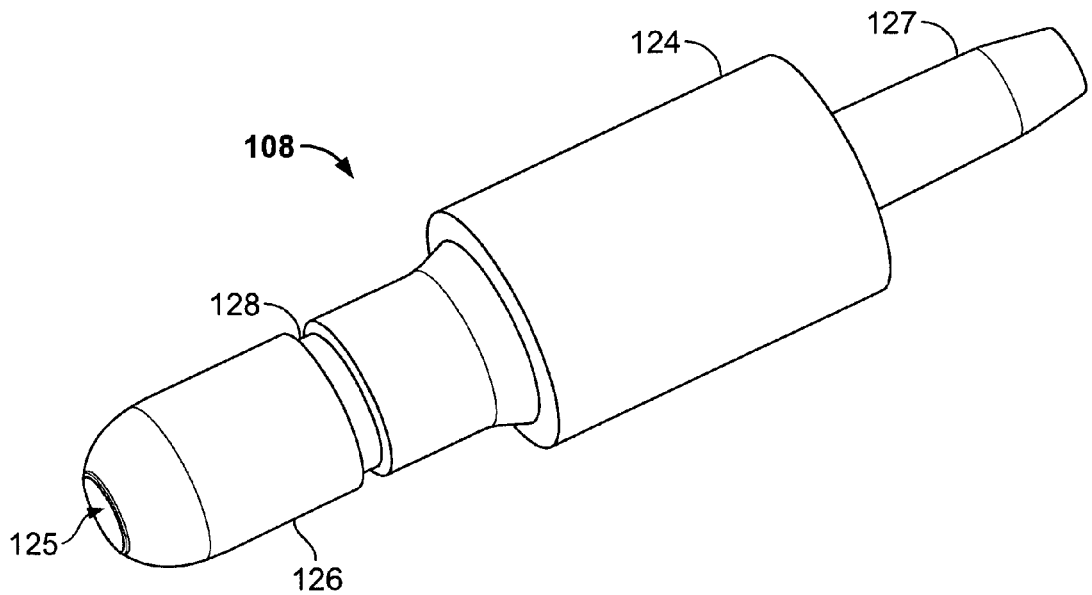
FIG. 3 is a perspective view of the plug member of the tube connector of FIG. 1 according to the present invention.

As shown in FIG. 3, plug member 108 has a base 124 and a stem 126. The base 124 is adapted to be attached to a tube (not shown) via a nipple 127. The stem 126 extends axially from the opposite end of the base 124. A passageway 125 extends through the plug member 108 between the base 124 and the stem 126 for conveying fluid/air. The stem 126 has a circumferential groove or channel 128 therein, and is adapted to be received within the latching component 106 (see FIG. 4). Latching component is preferably formed of an elastomeric material allowing deflection for securing parts of the tubing connector and providing a seal therebetween.

Figure 4:
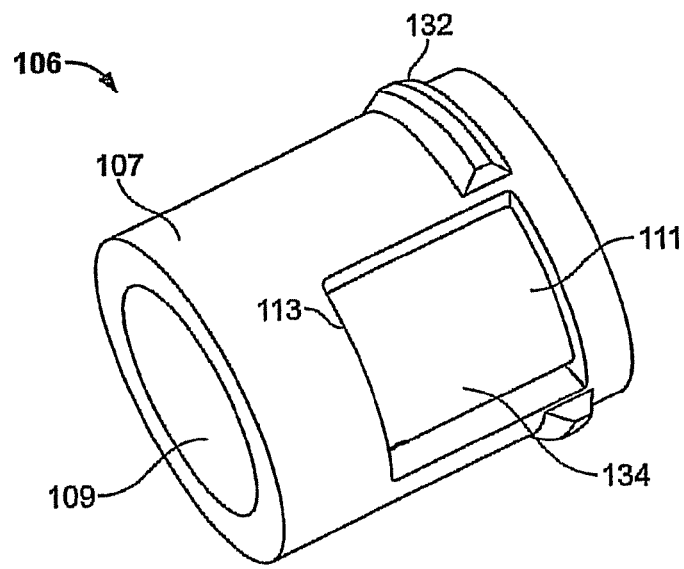
FIG. 4 is a perspective view of the latching component of the tube connector of FIG. 1 according to the present invention.

The latching component 106 of FIG. 4 is in the form of a sleeve sized and shaped to receive the stem 126 of plug member 108 therein, and in turn to be received in the first portion 118 of bore 116 of receptacle 102. Latching component 106 includes an interior surface 109 and exterior surface 107, exterior surface 107 having a circumferential ridge 132 thereon; here, one ridge 132 does not go completely around the circumference. Latching component 106 further includes two resilient tabs 134 spaced diametrically opposite one another, although any number of tabs is contemplated. The tabs 134 are connected (e.g., made integral) at one end 113 to the latch component 106 in a hinge-like arrangement. The free end 111 of each resilient tab 134 has a rib 136 (FIG. 5) extending past the inside surface 109 and slightly within the interior of the latching component 106. The ridge 132, which is a partial ring, engages with the groove 122 of the first interior surface 112 of the receptacle 102 when the latching component 106 is inserted into the first portion 118 through bore 116 of receptacle 102. The rib 136 is arranged to resiliently engage with circumferential channel 128 on stem 126 of plug member 108 when inserting plug member 108 into latching component 106.

Figure 5:
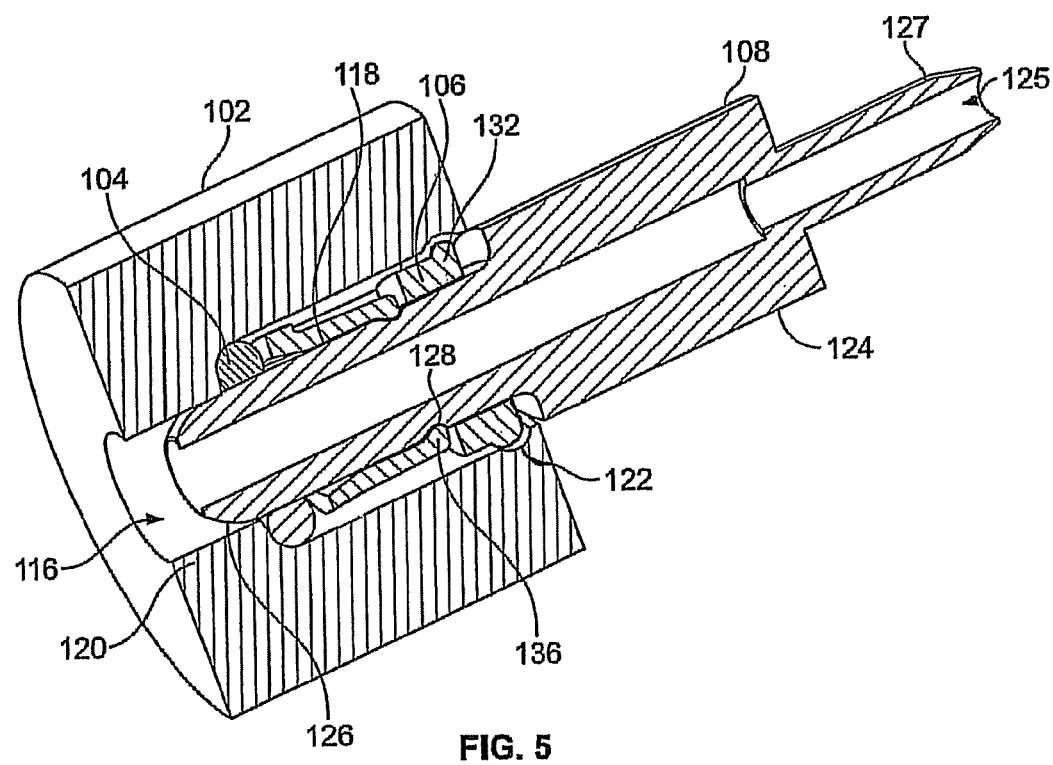
FIG. 5 is an assembled cross-sectional view of the tube connector of FIG. 1 according to the present invention.

One manner of assembly of the receptacle 102, sealing ring 104, latching component 106 and plug member 108 is shown in FIG. 5. Sealing ring 104 is inserted axially into the first portion 118 of bore 116 of the receptacle 102. The sealing ring 104 has an outer diameter D1 that fits within first portion 118 of bore 116, and greater than D2 of second portion 120 of bore 116 such that sealing ring 104 abuts the second portion 120 of bore 116. The latching component 106 is then inserted into the first portion 118 of bore 116 abutting sealing ring 104 forming an airtight seal, and circumferential ridge 132 engages with the groove 122 of the first interior surface 112 of the receptacle 102. The latching component 106 is secured within receptacle 102 in a manner such that the latching component 106 does not move axially within receptacle 102, although it is contemplated that the latching component 106 and receptacle 102 could have a rotatable engagement. The stem 126 of the plug member 108 is inserted into latching component 106. The ribs 136 on tabs 134 resiliently engage with the circumferential channel 128 on stem 126 which secures the plug member 108 within latching component 106 and thus within receptacle 102. The engagement between ribs 136 and the circumferential channel 128 is such that the plug member 108 can rotate generally freely within the latching component 106. Latching component is preferably formed of a plastic material.

As shown in FIGS. 6-8, receptacle 102 can be formed integrally with the motor drive unit of a breast pump assembly. Assembly of the tube connector 100 in this embodiment is similar to that described above. Sealing ring 104 is inserted axially into the first portion 118 of bore 116 of the receptacle 102 such that sealing ring 104 abuts the second portion 120 of bore 116. The latching component 106 is inserted as previously described with circumferential ridge 132 engaging with the groove 122, securing the latching component 106 within receptacle 102. Plug member 108 can then be releasably inserted into latching component 106, with tabs 134 resiliently engaging with the circumferential channel 128 on stem 126, to secure the plug member 108 within latching component 106 and thus within receptacle 102.

Figure 9:
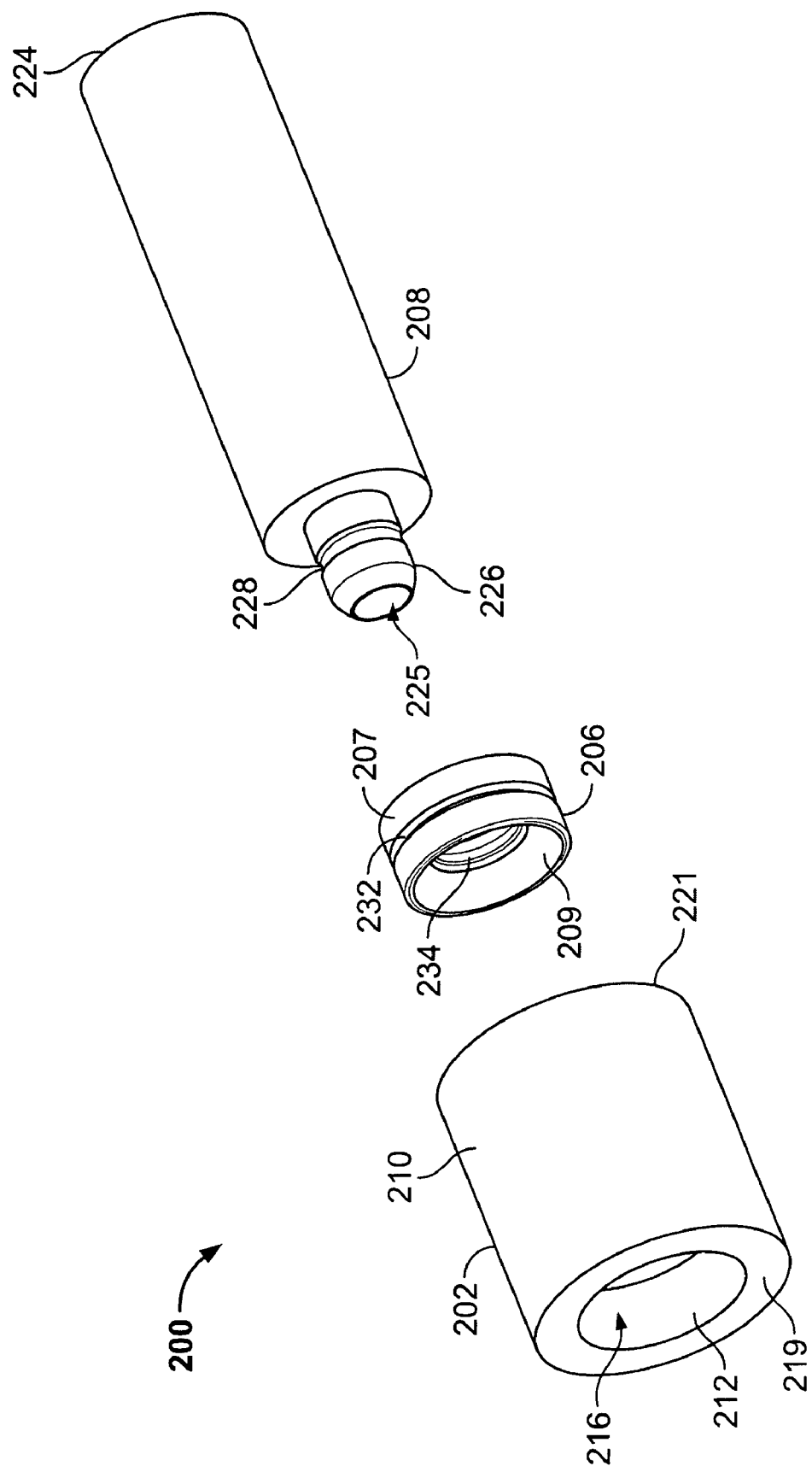
FIG. 9 is an exploded perspective view of an alternate embodiment of a tube connector according to the present invention.

FIG. 9 is an exploded view of a second embodiment of a tubing connector 200 according to the present invention. This second embodiment tubing connector 200 includes a receptacle 202, a latching component 206 and a plug member 208.

Figure 10:
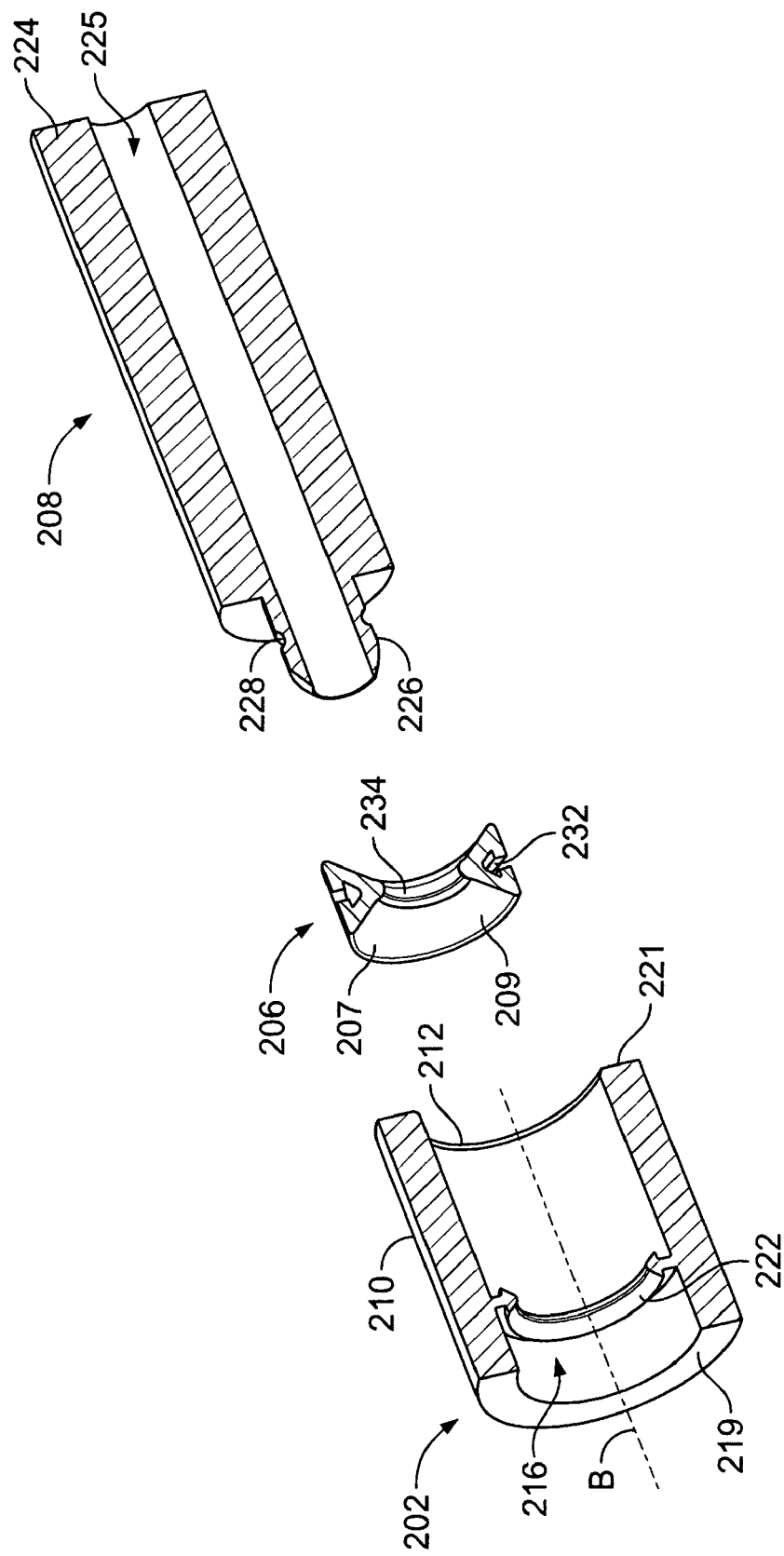
FIG. 10 is an exploded sectional view of the alternate embodiment of the tube connector of FIG. 9 according to the present invention.

As shown in FIG. 10, this receptacle 202 has an exterior surface 210 and an interior surface 212, interior surface 212 defining a bore 216 therethrough. An axis B is defined extending into bore 216. The interior surface 212 has a ring or protrusion 222 thereon around its entire circumference. Receptacle 202 includes two ends 219, 221. The first end 219 of receptacle 202 is adapted, for instance, to be connected to a motor drive unit of a breast pump assembly, or formed integrally therewith. The second end 221 of receptacle 202 receives other components of tube connector 200 therein as will be described in detail.

Also shown in FIG. 10, plug member 208 is adapted at one end 224 to be attached to a tube (not shown). The tube could then be formed integral therewith, or otherwise connected to passageway 225. A stubby stem 226 extends axially from the opposite end of base 224. Passageway 225 extends through the plug member 208 between the end 224 and the stem end 226 for conveying fluid/air. The stem 226 has a circumferential groove or channel 228 therein adapted to be received within the latching component 206.

Figure 11:
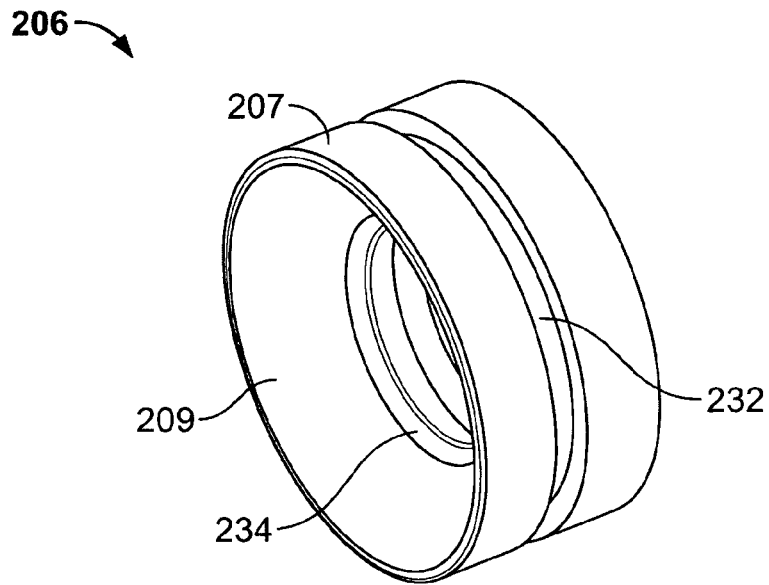
FIG. 11 is a perspective view of the latch portion of the alternate embodiment of the tube connector of FIG. 9 according to the present invention.
Figure 12:
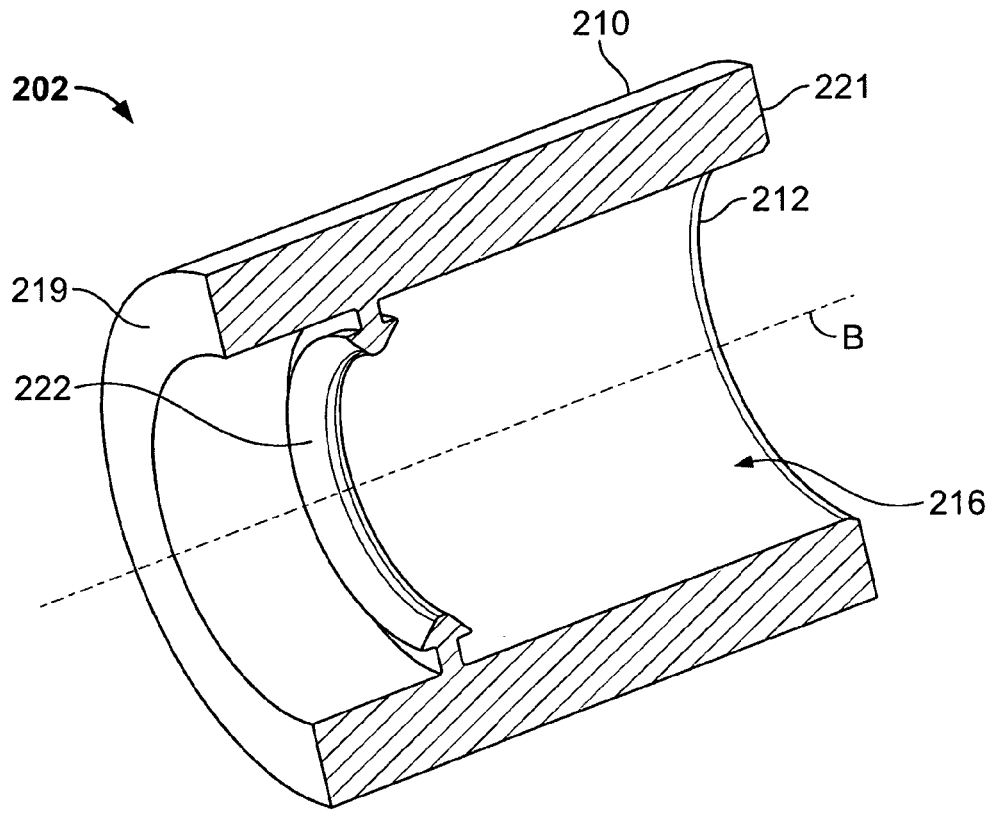
FIG. 12 is a perspective sectional view of the receptacle of the alternate embodiment of the tube connector of FIG. 9 according to the present invention.
Figure 13:
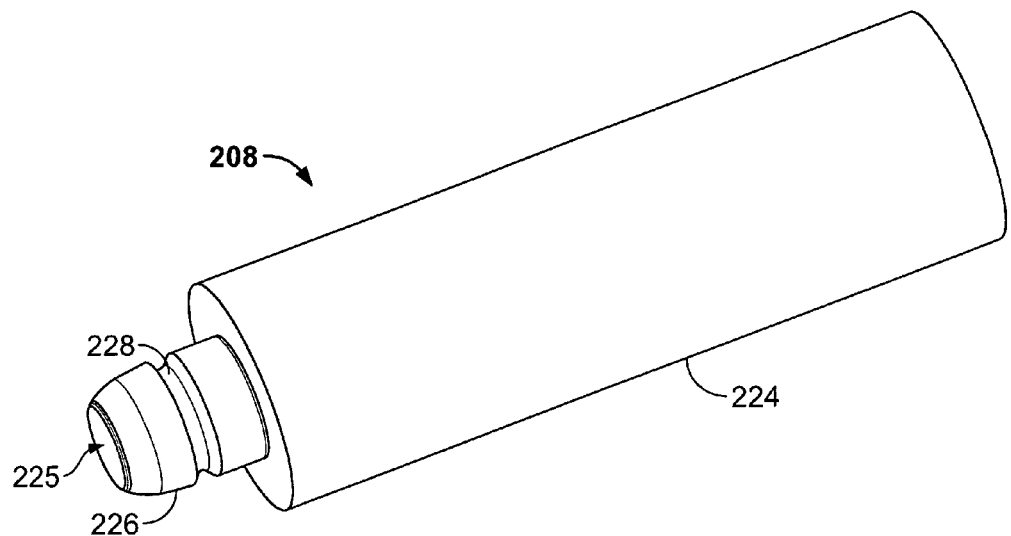
FIG. 13 is a perspective view of the plug member of the alternate embodiment of the tube connector of FIG. 9 according to the present invention.

Referring to FIG. 11, this latching component 206 is likewise in the form of a sleeve sized and shaped to receive the stem 226 of plug member 208 therein, and to be received in the bore 216 in this type of receptacle 202. Modified latching component 206 includes an interior surface 209 and exterior surface 207. Exterior surface 207 has a circumferential groove or channel 232 thereon that engages with the ring 222 on the interior surface 212 of the receptacle 202 (FIG. 12) when the latching component 206 is inserted into the bore 216 in receptacle 202. Latching component 206 further includes a rib or ridge 234 on its interior 209 sized and shaped to match (FIG. 13) the circumferential groove 228 of stem 226 of plug member 208, such that when plug member 208 is inserted into latching component 206, rib 234 engages circumferential groove 228, which rotatably secures plug member 208 within latching component 206.

Figure 14:
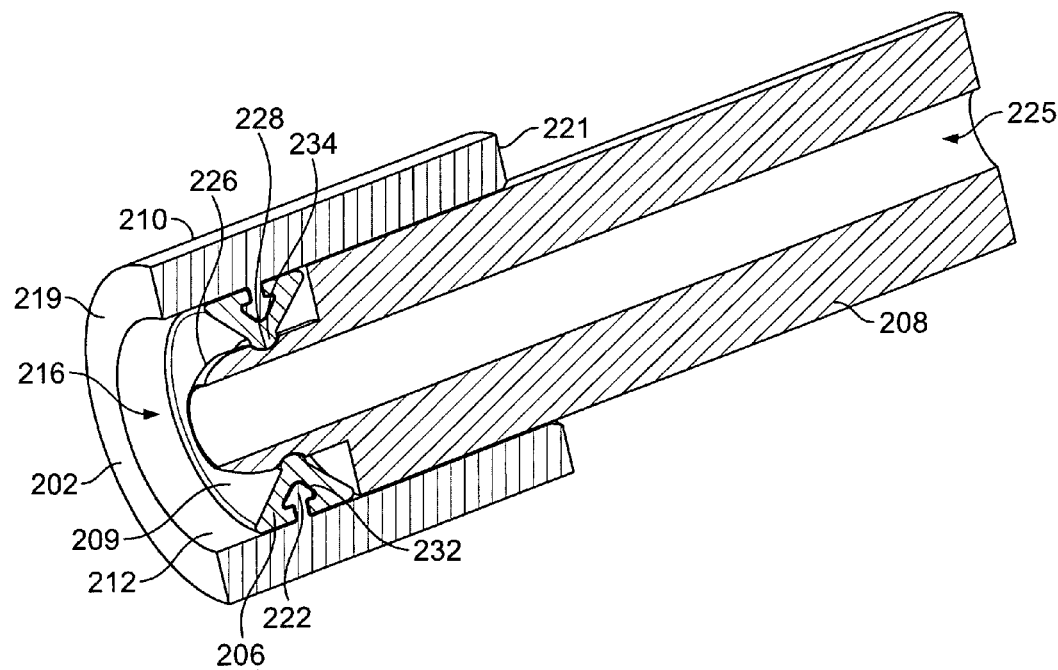
FIG. 14 is an assembled sectional view of the alternate embodiment of the tube connector of FIG. 9 according to the present invention.

This is shown in FIG. 14, where latching component 206 is inserted axially into the bore 216, and groove 232 engages with the protrusion 222 on the interior surface 212 of the receptacle 202 which secures the latching component 206 within receptacle 202. The stem 226 of the plug member 208 is inserted into latching component 206 and the rib 234 engages with the circumferential groove 228 on stem 226 which secures the plug member 208 within latching component 206 and thus within receptacle 202. The engagement between the rib 234 and the circumferential groove 228 is such that the plug member 208 can rotate freely within the latching component 206. Latching component is preferably formed of an elastomeric material allowing deflection for securing parts of the tubing connector and providing a seal therebetween.

Figure 15:
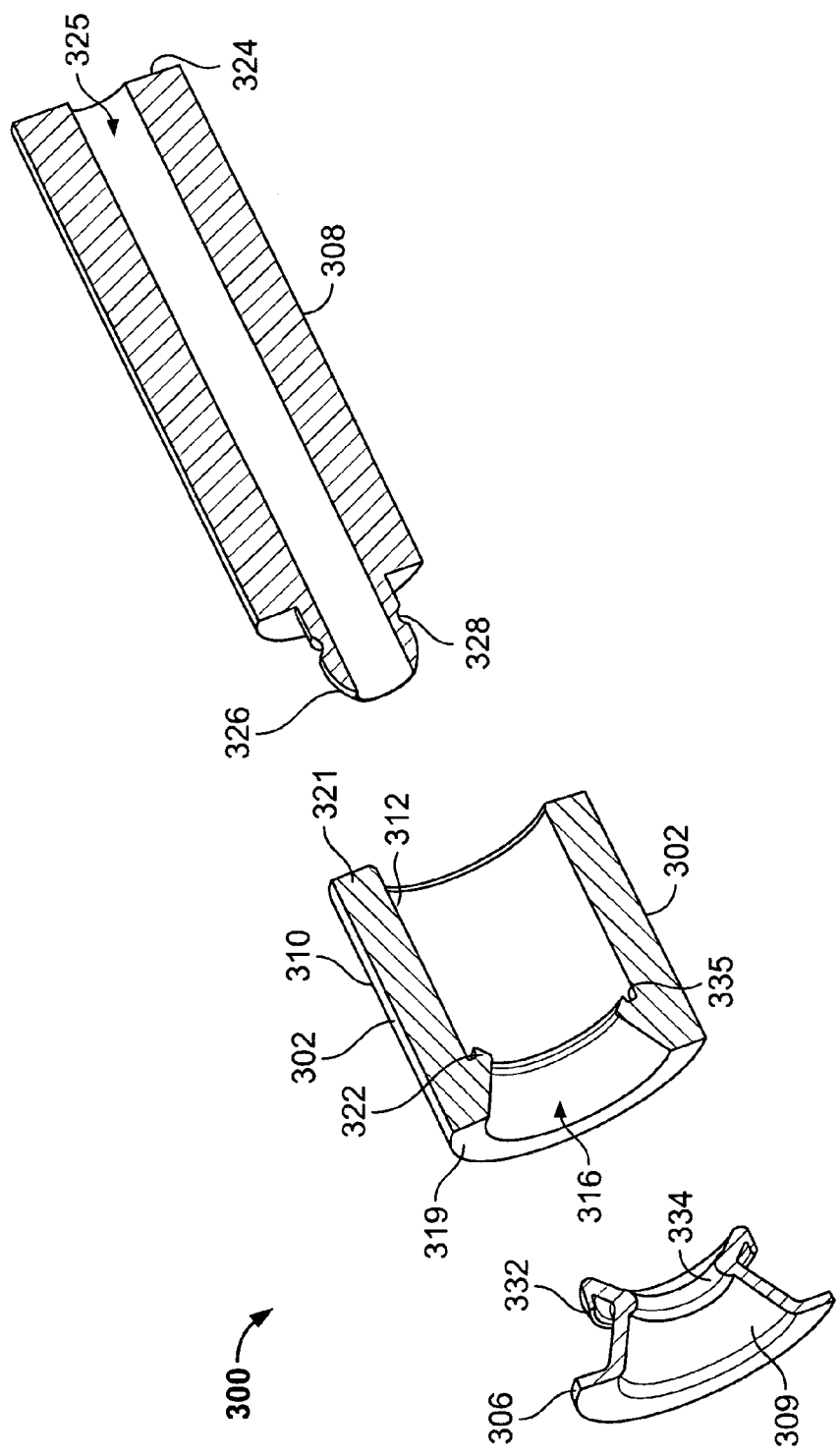
FIG. 15 is an exploded sectional view of yet another alternate embodiment of a tube connector according to the present invention.
Figure 16:
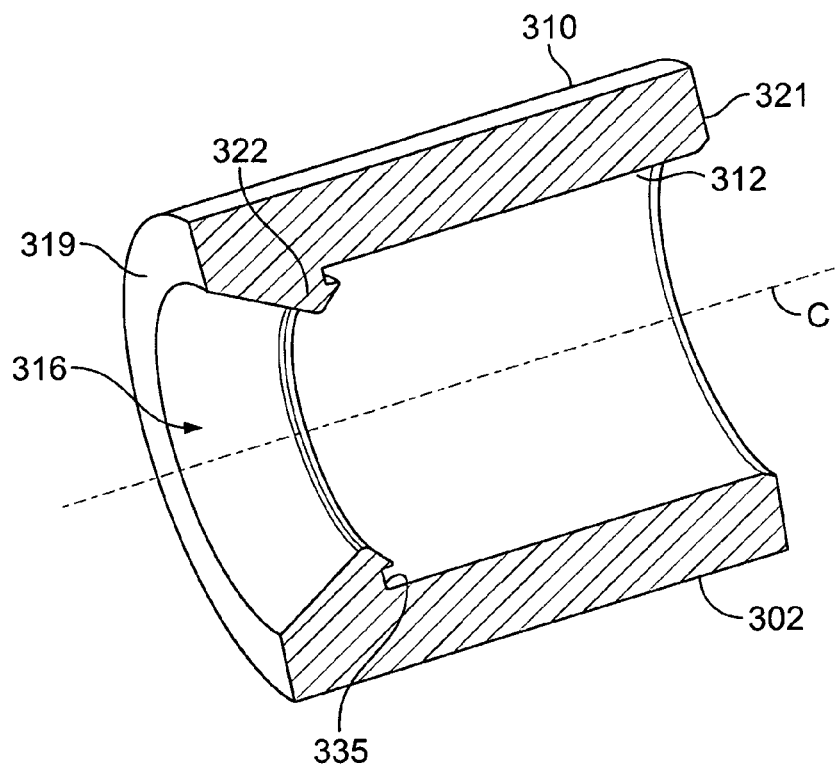
FIG. 16 is a perspective sectional view of the receptacle of an alternate embodiment of the tube connector of FIG. 15 according to the present invention.

FIG. 15 is an exploded view of a third embodiment of a tubing connector 300 according to the present invention. This third embodiment tubing connector 300 includes a receptacle 302, a latching component 306 and a plug member 308. As shown in FIG. 16, receptacle 302 has an exterior surface 310 and an interior surface 312, interior surface 312 defining a bore 316 therethrough. An axis C is defined extending into bore 316. The interior surface 312 has a circumferential lip 322 thereon around its entire circumference. Receptacle 302 includes two ends 319, 321. The first end 319 of receptacle 302 is adapted, for instance, to be connected to a motor drive unit of a breast pump assembly, or formed integrally therewith. The second end 321 of receptacle 302 receives other components of tube connector 300 therein as will be described in detail.

Figure 17:
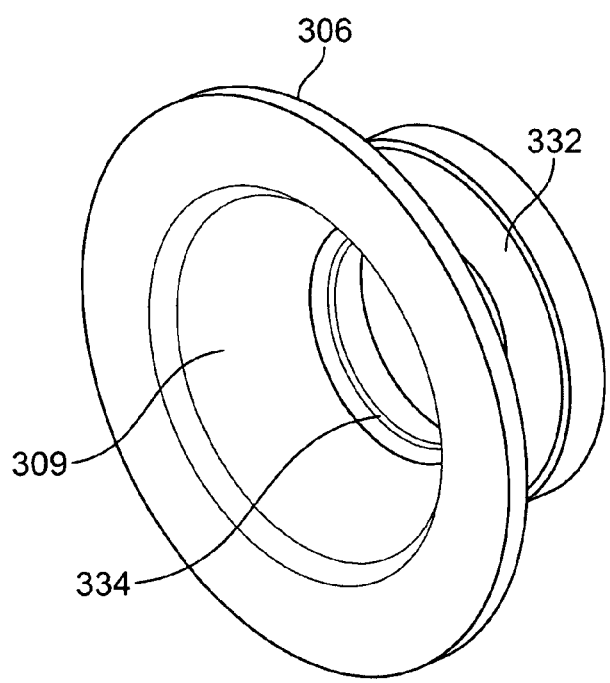
FIG. 17 is a perspective view of a latch portion of an alternate embodiment of the tube connector of FIG. 15 according to the present invention.

Turing to FIG. 17, latching component 306 includes an interior surface 309 and a circumferential groove or channel 332 on the outboard side. Groove 332 is annular in form, being located beneath an overlying lip 333. Latching component 306 further includes a shoulder 334 on its interior 309 sized and shaped to match the circumferential groove 328 (FIG. 15) in stem 326 of plug member 308 such that when plug member 308 is inserted into latching component 306 (FIG. 18), shoulder 334 engages circumferential groove 328, which secures plug member 308 within latching component 306.

Figure 18:
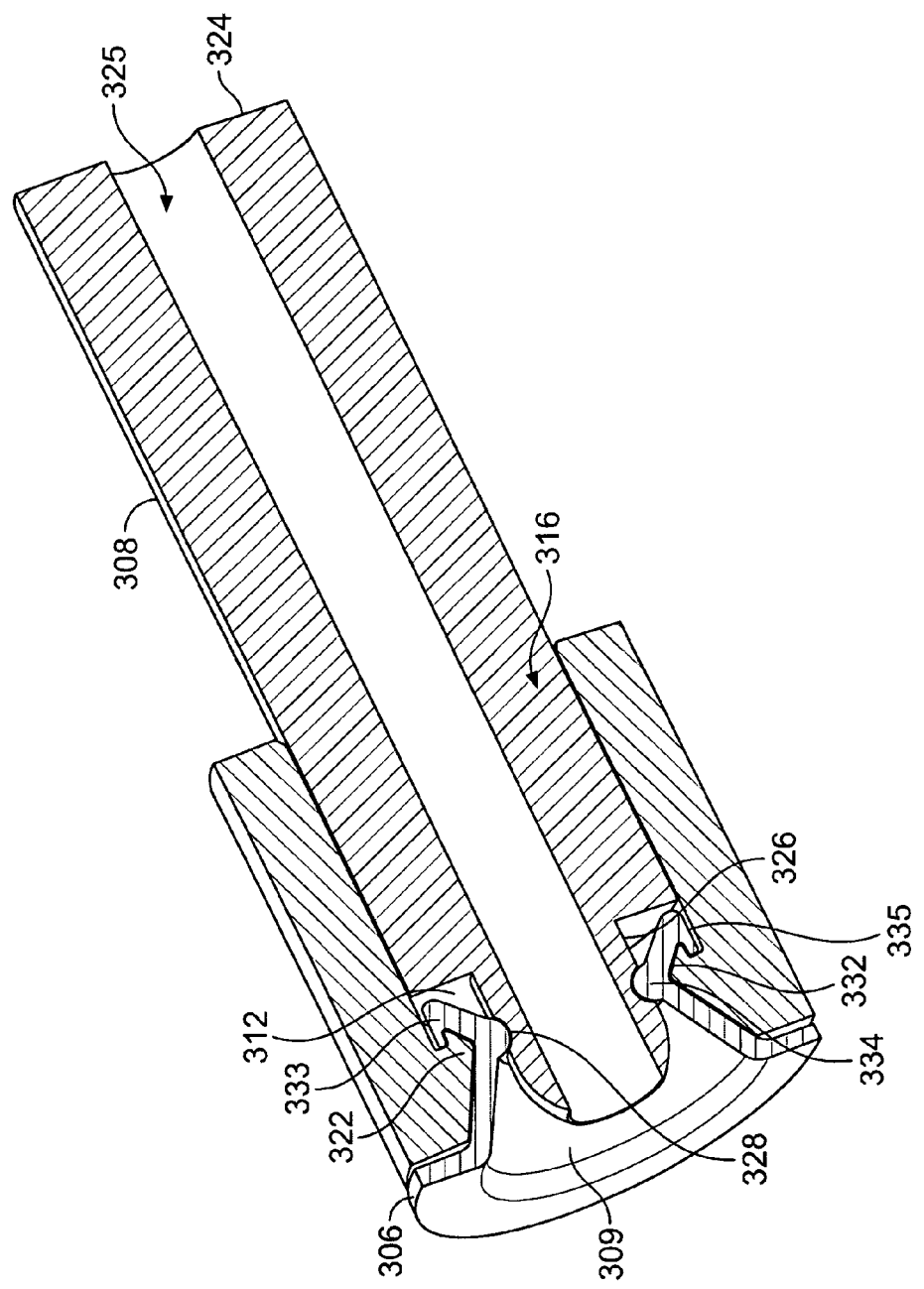
FIG. 18 is an assembled sectional view of the alternate embodiment of the tube connector of FIG. 15 according to the present invention.

As further shown in FIG. 18, plug member 308 has an end 324 adapted to be attached to a tube (not shown) in any number of well known ways. A stem 326 (FIG. 15) extends axially from the opposite end of the plug member 308. A passageway 325 extends through the plug member 308 between the base 324 and the stem 326 for conveying fluid/air.

Latching component 306 is sized and shaped to receive the stem 326 of plug member 308 therein, and to be received in the bore 316 in receptacle 302. The groove 332 of latching component 306 engages with the lip 322 along the interior surface 312 of the receptacle 302, with lip 333 thereby snapping into place within a channel 335 formed between the lip 322 and adjacent sidewall of the receptacle 302 when the latching component 306 is inserted into the bore 316 in receptacle 302. This is a snap-fit between the receptacle 302 and latching component 306, and these elements are so sized to thus engage.

In one manner of assembly, latching component 306 is inserted axially into the bore 316, and groove 332 engages with the lip 322 on the interior surface 312 of the receptacle 302 which secures the latching component 306 within receptacle 302. The stem 326 of the plug member 308 is inserted into the combined latching component 306 and receptacle 302, and the shoulder 334 engages with the circumferential groove 328 on stem 326, thus securing the plug member 308 within latching component 306 and within receptacle 302. The engagement between the shoulder 334 and the circumferential groove 328 is such that the plug member 308 can rotate freely within the latching component 306. Latching component is preferably formed of an elastomeric material allowing deflection for securing parts of the tubing connector and providing a seal therebetween.

Figure 19:
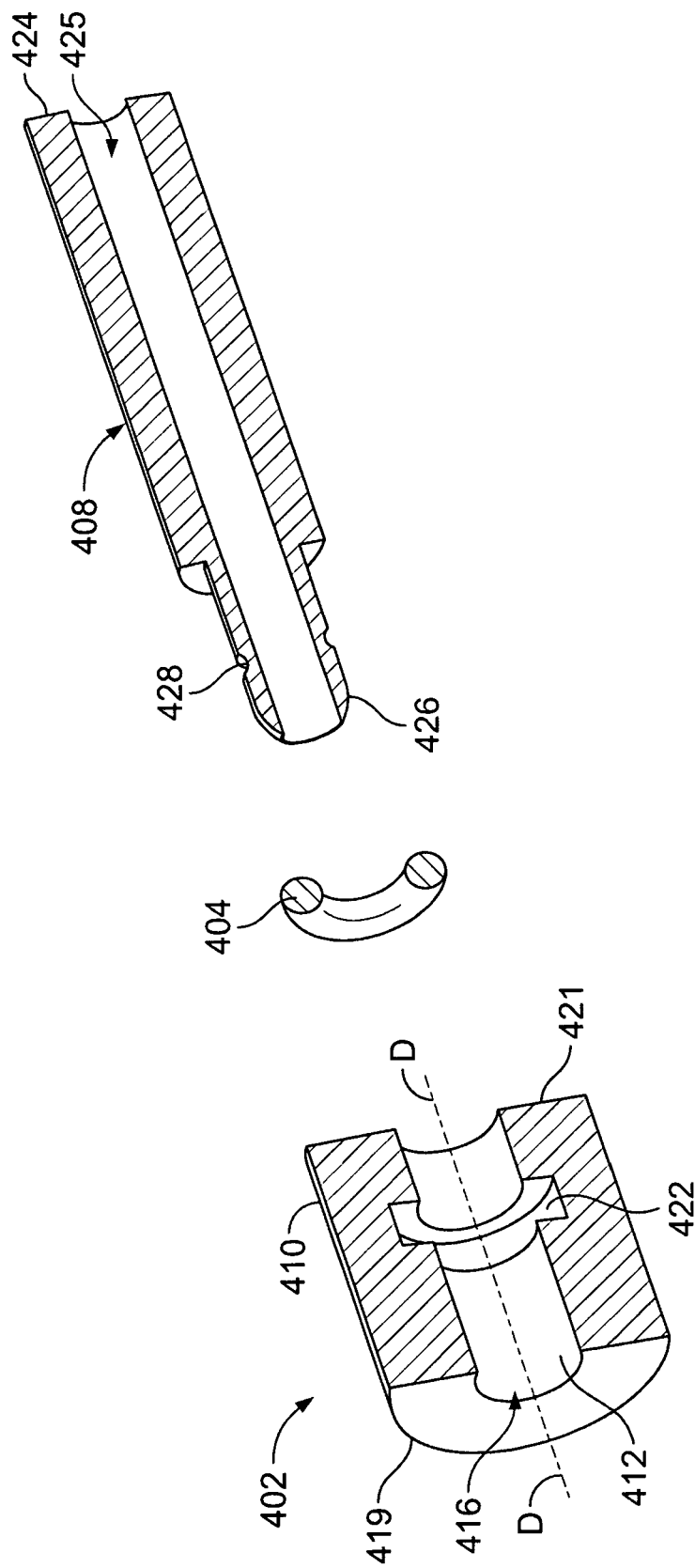
FIG. 19 is a perspective sectional view of an alternate embodiment of a tube connector according to the present invention.
Figure 20:
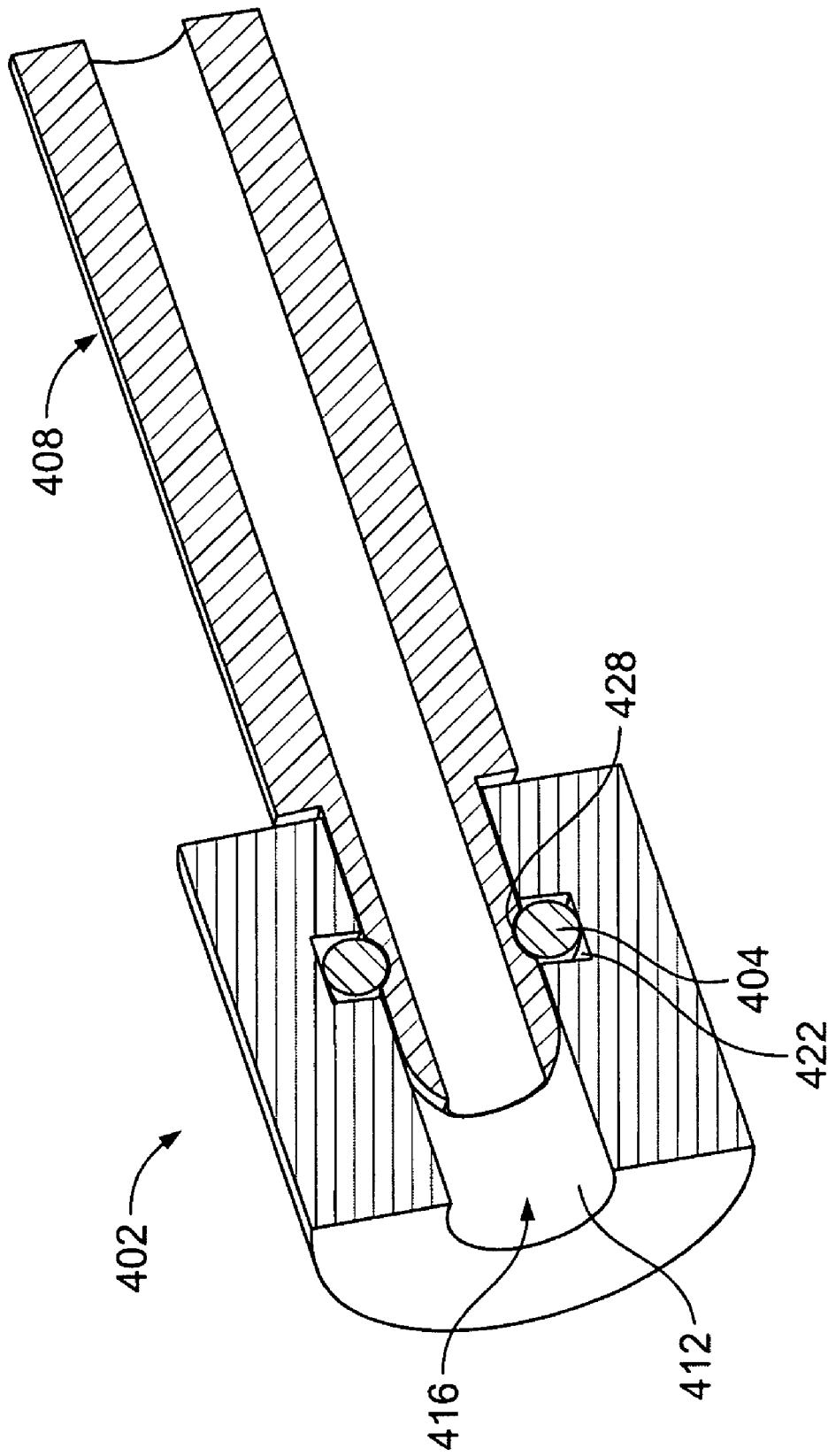
FIG. 20 is an assembled sectional view of the alternate embodiment of the tube connector of FIG. 19 according to the present invention.

Yet another embodiment of the present invention is depicted in FIGS. 19-20. As shown in FIG. 19, receptacle 402 has an exterior surface 410, and an interior surface 412. The interior surface 412 defines a bore 416 therethrough. An axis D extends into bore 416. A circumferential groove 422 is formed around the interior surface 412. Receptacle 402 includes two ends 419, 421. The first end 419 of receptacle 402 is adapted, for instance, to be connected to a motor drive unit of a breast pump assembly, or formed integrally therewith. The second end 421 of receptacle 402 receives other components of yet another tube connector therein, as will be described in detail below.

The plug member 408 has an end 424 and a stem 426. The end 424 is adapted to be attached to a tube (not shown) in any of many known ways. The stem 426 extends axially from the opposite end of the base 424. A passageway 425 extends through the plug member 408 between the end 424 and the stem 426 for conveying fluid/air.

As further shown in FIG. 20, sealing member 404 is sized to fit in the circumferential groove 422 of the interior surface 412 of the receptacle 402. This seal member 404 engages the circumferential groove 428 of the plug member 408 when plug member 408 is inserted into the bore 416 of the receptacle 402 thereby forming an air-tight seal, acting to retain the plug member 408 within the receptacle 402 by resisting removal forces, and also allowing the plug member 408 to rotate freely within the receptacle 402. It will be understood that the receptacle 402 could be integral with a housing and further include a shoulder surface on the interior 412, similar to embodiments previously described, for engagement with a plug member. Furthermore, a component retained within the bore, or a surface integral with the receptacle, could define and function as a sealing member. There are many contemplated embodiments that serve to simplify fabrication and assembly.

It is understood that all shapes and sizes, configurations of the tube connector are contemplated by the invention and are considered various embodiments thereof.

It is seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense. It is also to be understood that the following claims are intended to cover all of the generic and specific features of the invention herein described and all statements of the scope of the invention that, as a matter of language, might be said to fall there between.

While the apparatus and method herein disclosed forms a preferred embodiment of this invention, this invention is not limited to that specific apparatus and method, and changes can be made therein without departing from the scope of this invention, which is defined in the appended claims.

What is claimed is:

1. A tubing connector, comprising:
   an elongated plug having an exterior, a forward end and a channel formed therethrough,
   a receptacle within which said plug forward end is receivable, said receptacle having a bore formed therein with an interior surface defined within said bore,
   a male engagement member formed on and within said receptacle bore,
   a female engagement member formed on said plug exterior,
   a latching component being sized and shaped to be assembled within said receptacle, said latching component having an exterior wall and a throughbore defined within said latching component which axially aligns with said receptacle bore when assembled,
   a second female engagement member formed on said exterior wall of said latching component, said second female engagement member sized and shaped to be received by said male engagement member, and
   a second male engagement member formed on said latching component, said second male engagement member sized and shaped to be received by said female engagement member of said plug forward end,
   said second male engagement member and said female engagement member mating when said plug forward end is received within said latching component, said male engagement member and said second female engagement member mating in releasable engagement when said latching component is received within said receptacle bore with said members aligned.

2. The tubing connector of claim 1 wherein said male engagement member is a circumferential ring and said female engagement member is a circumferential channel.

3. The tubing connector of claim 2 wherein said circumferential channel is formed on said plug exterior, and said circumferential ring is formed on said receptacle bore.

4. The tubing connector of claim 3 wherein said male and female engagement members engage in a substantially fluid tight fit with said latching component.

5. The tubing connector of claim 3 wherein said male and female engagement members engage with said latching component in a manner that leaves them rotatable relative to one another.

6. The tubing connector of claim 1 wherein said male and female members and said second male and second female engagement members engage to provide a substantially fluid tight fit between said plug and receptacle.

7. The tubing connector of claim 6 wherein said male and female members engage in a manner that leaves the latching component and plug rotatable relative to one another.

8. The tubing connector of claim 1 wherein said latching component is not removable in normal use of said connector after assembly with said receptacle.

9. The tubing connector of claim 2 wherein said engagement is a snap fit.

10. A tubing connector, comprising:
    an elongated plug having an exterior, a forward end and a channel formed therethrough,
    a receptacle, said receptacle having a bore formed therein with a first interior surface and
    a latching component, said latching component adapted to be assembled within said bore of said receptacle when inserted therein, said latching component having an exterior wall and a throughbore defined within said latching component which axially aligns with said receptacle bore when assembled,
    a first male engagement member formed within said latching component on said throughbore,
    a first female engagement member formed on said plug exterior, said first male and female engagement members mating in releasable engagement when said plug forward end is received within said latching component with said members aligned therein,
    a second female engagement member formed on said first interior surface of said receptacle,
    a second male engagement member formed on said exterior wall of said latching component,
    said second male and female engagement members mating when said latching component is received within said receptacle with said second engagement members aligned therein.

11. The tubing connector of claim 10 wherein said first female engagement member is a circumferential channel.

12. The tubing connector of claim 11 wherein said first male and female engagement members and said second male and second female engagement members respectively engage to provide a substantially fluid tight fit between said plug and receptacle.

13. The tubing connector of claim 12 wherein said second male and second female engagement members engage in a manner that leaves the latching component and plug rotatable relative to one another.

14. The tubing connector of claim 10 wherein said first male engagement member is formed on at least one tab and said female engagement member is a circumferential channel.

15. The tubing connector of claim 14 wherein said circumferential channel is formed on said plug exterior, and said at least one tab is formed on said latching component.

16. The tubing connector of claim 15 wherein there is a pair of opposed tabs.

17. The tubing connector of claim 16 wherein said latching component is not removable in normal use of said connector after assembly with said receptacle.

18. A tube connector, comprising:
a receptacle having a throughbore and annular groove defined therein;
a sealing member that is positioned within said receptacle;
a latching component that is separate from the receptacle, having a throughbore, a female end and a male end, said female end includes at least one tab extending therefrom, said at least one tab having a rib thereon, said latching component further including an external ridge that engages with said annular groove of said receptacle whereby said latching component is retained within said receptacle;
an elongated plug having an interior channel therethrough and
a stem at one end, said plug having another end for connection to tubing, said stem having an annular groove therein that engages with said rib on said at least one tab of said latching component, wherein said plug component is rotatably received and releasably held within said latching component.

19. The adapter of claim 18 wherein said sealing member is an O-ring.

20. The adapter of claim 18 wherein said receptacle is integrally formed with a breast pump assembly.

* * * * *

UNITED STATES PATENT AND TRADEMARK OFFICE
CERTIFICATE OF CORRECTION

PATENT NO. : 7,780,201 B2
APPLICATION NO. : 11/581210
DATED : August 24, 2010
INVENTOR(S) : Mark A. Luzbetak and Donald C. Walker It is certified that error appears in the above-identified patent and that said Letters Patent is hereby corrected as shown below:

At column 8, line 32, please delete the phrase "tight fit between said plug and receptacle" and add the phrase -- tight fit between said plug and said receptacle --

At column 8, line 45, please delete the phrase "and" and add the phrase -- , --

At column 8, line 60, please delete the phrase "interior surface of said receptacle," and add the phrase -- interior surface of said receptacle, and --

At column 10, line 5, please delete the phrase "the" and add the phrase -- said --

At column 10, line 7, please delete the phrase "includes" and add the phrase -- including --

At column 10, line 13, please delete the phrase "an elongated plug having an interior channel therethrough" and add the phrase -- an elongated plug having an interior channel therethrough, --

Signed and Sealed this

Seventh Day of December, 2010

David J. Kappos
*Director of the United States Patent and Trademark Office*